(12) United States Patent
Miller et al.

(10) Patent No.: US 10,857,526 B2
(45) Date of Patent: *Dec. 8, 2020

(54) CRYSTALLINE TRANSITION METAL TUNGSTATE PROCESS DATA SYSTEM

(71) Applicant: UOP LLC, Des Plaines, IL (US)

(72) Inventors: Stuart R. Miller, Arlington Heights, IL (US); Susan C. Koster, Carpentersville, IL (US)

(73) Assignee: UOP LLC, Des Plaines, IL (US)

( * ) Notice: Subject to any disclaimer, the term of this patent is extended or adjusted under 35 U.S.C. 154(b) by 121 days.

This patent is subject to a terminal disclaimer.

(21) Appl. No.: 16/110,237

(22) Filed: Aug. 23, 2018

(65) Prior Publication Data

US 2019/0060879 A1 Feb. 28, 2019

Related U.S. Application Data

(60) Provisional application No. 62/550,256, filed on Aug. 25, 2017.

(51) Int. Cl.
| | |
|---|---|
| *B01J 23/888* | (2006.01) |
| *G16C 20/70* | (2019.01) |
| *B01J 27/049* | (2006.01) |
| *G05B 15/02* | (2006.01) |
| *C10G 45/72* | (2006.01) |

(Continued)

(52) U.S. Cl.
CPC .......... *B01J 23/888* (2013.01); *B01J 27/049* (2013.01); *B01J 37/0009* (2013.01); *B01J 37/009* (2013.01); *B01J 37/0018* (2013.01); *B01J 37/031* (2013.01); *B01J 37/033* (2013.01); *B01J 37/04* (2013.01); *B01J 37/06* (2013.01); *B01J 37/08* (2013.01); *B01J 37/20* (2013.01); *C01G 41/00* (2013.01); *C01G 41/02* (2013.01); *C01G 53/00* (2013.01); *C01G 53/40* (2013.01); *C10G 45/72* (2013.01); *C10G 47/36* (2013.01); *G05B 15/02* (2013.01); *G16C 20/70* (2019.02); *G16C 20/90* (2019.02); *B01J 2523/00* (2013.01); *B01J 2523/69* (2013.01); *B01J 2523/845* (2013.01); *B01J 2523/847* (2013.01);

(Continued)

(58) Field of Classification Search
None
See application file for complete search history.

(56) References Cited

U.S. PATENT DOCUMENTS

| | | | |
|---|---|---|---|
| 2012/0191288 A1* | 7/2012 | Qi | B01D 53/9495 701/29.1 |
| 2019/0126251 A1* | 5/2019 | Serban | B01J 35/1085 |
| 2019/0126256 A1* | 5/2019 | Serban | C07C 5/3337 |

* cited by examiner

*Primary Examiner* — Tam M Nguyen

(57) ABSTRACT

A hydroprocessing catalyst has been developed. The catalyst is a crystalline transition metal tungstate material or metal sulfides derived therefrom, or both. The hydroprocessing using the crystalline transition metal tungstate material may include hydrodenitrification, hydrodesulfurization, hydrodemetallation, hydrodesilication, hydrodearomatization, hydroisomerization, hydrotreating, hydrofining, and hydrocracking. A data system comprising at least one processor; at least one memory storing computer-executable instructions; and at least one receiver configured to receive data of at least one unit or stream in fluid communication with and downstream from or upstream to a conversion process comprising at least one reaction catalyzed by the catalyst or a metal sulfide decomposition product of the catalyst has been developed.

8 Claims, 3 Drawing Sheets

(51) Int. Cl.
*C10G 47/36* (2006.01)
*C01G 53/00* (2006.01)
*B01J 37/08* (2006.01)
*B01J 37/03* (2006.01)
*B01J 37/06* (2006.01)
*C01G 41/00* (2006.01)
*G16C 20/90* (2019.01)
*B01J 37/00* (2006.01)
*B01J 37/04* (2006.01)
*B01J 37/20* (2006.01)
*C01G 41/02* (2006.01)
*G16C 20/10* (2019.01)
*C10G 45/50* (2006.01)

(52) U.S. Cl.
CPC ...... *C01P 2002/72* (2013.01); *C01P 2002/74* (2013.01); *C10G 45/50* (2013.01); *G16C 20/10* (2019.02)

CRYSTALLINE TRANSITION METAL TUNGSTATE PROCESS DATA SYSTEM

CROSS-REFERENCE TO RELATED APPLICATION

This application claims priority from U.S. Provisional Application No. 62/550,256 filed Aug. 25, 2017, the contents of which cited application are hereby incorporated by reference in its entirety.

FIELD OF THE INVENTION

This invention relates to a new hydroprocessing catalyst. More particularly this invention relates to a crystalline transition metal tungstate and metal sulfides derived therefrom, and their use as a catalyst such as a hydrocarbon conversion catalyst or specifically a hydroprocessing catalyst. The hydroprocessing may include hydrodenitrification, hydrodesulfurization, hydrodemetallation, hydrodesilication, hydrodearomatization, hydroisomerization, hydrotreating, hydrofining, and hydrocracking.

BACKGROUND

In order to meet the growing demand for petroleum products there is greater utilization of sour crudes, which when combined with tighter environmental legislation regarding the concentration of nitrogen and sulfur within fuel, leads to accentuated refining problems. The removal of sulfur (hydrodesulfurization—HDS) and nitrogen (hydrodenitrification—HDN) containing compounds from fuel feed stocks is targeted during the hydrotreating steps of refining and is achieved by the conversion of organic nitrogen and sulfur to ammonia and hydrogen sulfide respectively.

Since the late 1940s the use of catalysts containing nickel (Ni) and molybdenum (Mo) or tungsten (W) have demonstrated up to 80% sulfur removal. See for example, V. N. Ipatieff, G. S. Monroe, R. E. Schaad, Division of Petroleum Chemistry, 115$^{th}$ Meeting ACS, San Francisco, 1949. For several decades now there has been an intense interest directed towards the development of materials to catalyze the deep desulfurization, in order to reduce the sulfur concentration to the ppm level. Some recent breakthroughs have focused on the development and application of more active and stable catalysts targeting the production of feeds for ultra low sulfur fuels. Several studies have demonstrated improved HDS and HDN activities through elimination of the support such as, for example, $Al_2O_3$. Using bulk unsupported materials provides a route to increase the active phase loading in the reactor as well as providing alternative chemistry to target these catalysts.

More recent research in this area has focused on the ultra deep desulfurization properties achieved by a Ni—Mo/W unsupported 'trimetallic' material reported in, for example, U.S. Pat. No. 6,156,695. The controlled synthesis of a broadly amorphous mixed metal oxide consisting of molybdenum, tungsten and nickel, significantly outperformed conventional hydrotreating catalysts. The structural chemistry of the tri-metallic mixed metal oxide material was likened to the hydrotalcite family of materials, referring to literature articles detailing the synthesis and characterization of a layered nickel molybdate material, stating that the partial substitution of molybdenum with tungsten leads to the production of a broadly amorphous phase which, upon decomposition by sulfidation, gives rise to superior hydrotreating activities.

The chemistry of these layered hydrotalcite-like materials was first reported by H. Pezerat, contribution à l'étude des molybdates hydrates de zinc, cobalt et nickel, C. R. Acad. Sci., 261, 5490, who identified a series of phases having ideal formulas $MMoO_4.H_2O$, $EHM_2O^-(MoO_4)_2.H_2O$, and $E_{2-x}(H_3O)_xM_2O(MoO_4)_2$ where E can be $NH_4^+$, $Na^+$ or $K^+$ and M can be $Zn^{2+}$, $Co^{2+}$ or $Ni^{2+}$.

Pezerat assigned the different phases he observed as being Φc, Φy or Φy and determined the crystal structures for Φx and Φy, however owing to a combination of the small crystallite size, limited crystallographic capabilities and complex nature of the material, there were doubts raised as to the quality of the structural assessment of the materials. During the mid 1970s, Clearfield et al attempted a more detailed analysis of the Φx and Φy phases, see examples A. Clearfield, M. J. Sims, R. Gopal, Inorg. Chem., 15, 335; A. Clearfield, R. Gopal, C. H. Saldarriaga-Molina, Inorg. Chem., 16, 628. Single crystal studies on the product from a hydrothermal approach allowed confirmation of the Φx structure, however they failed in their attempts to synthesize Φy and instead synthesized an alternative phase, Na—Cu $(OH)(MoO_4)$, see A. Clearfield, A. Moini, P. R. Rudolf, Inorg. Chem., 24, 4606.

The structure of Φy was not confirmed until 1996 when by Ying et al. Their investigation into a room temperature chimie douce synthesis technique in the pursuit of a layered ammonium zinc molybdate led to a metastable aluminum-substituted zincite phase, prepared by the calcination of Zn/Al layered double hydroxide $(Zn_4Al_2(OH)_{12}CO_3.zH_2O)$. See example D. Levin, S. L. Soled, J. Y. Ying, Inorg. Chem., 1996, 35, 4191-4197. This material was reacted with a solution of ammonium heptamolybdate at room temperature to produce a highly crystalline compound, the structure of which could not be determined through conventional ab-initio methods. The material was indexed, yielding crystallographic parameters which were the same as that of an ammonium nickel molybdate, reported by Astier, see example M. P. Astier, G. Dji, S. Teichner, J. Ann. Chim. (Paris), 1987, 12, 337, a material belonging to a family of ammonium-amine-nickel-molybdenum oxides closely related to Pezerat's materials. Astier did not publish any detailed structural data on this family of materials, leading to Ying et al reproducing the material to be analyzed by high resolution powder diffraction in order to elucidate the structure. Ying et al named this class of materials 'layered transition-metal molybdates' or LTMs.

SUMMARY OF THE INVENTION

A crystalline transition metal tungstate material has been produced and optionally sulfided, to yield an active hydroprocessing catalyst. The crystalline transition metal tungstate material has a unique x-ray powder diffraction pattern showing peaks at 6.2, 3.5 and 3.1 Å. The crystalline transition metal tungstate material has the formula:

$$MW_xO_y$$

where 'M' is a metal selected from Mn, Fe, Co, Ni, V, Cu, Zn, Sn, Sb, Ti, Zr, and mixtures thereof; 'x' varies from 0.35 to 2, or from 0.75 to 1.5, or from 0.8 to 1.2; 'y' is a number which satisfies the sum of the valency of M and W; the material is further characterized by a unique x-ray powder diffraction pattern showing peaks at the d-spacings listed in Table A:

TABLE A

| d(Å) | I/I$_0$ (%) |
|---|---|
| 6.20 | s |
| 3.52 | vs |
| 3.12 | vs |
| 2.74 | vs |
| 2.41 | s |
| 2.33 | s |
| 2.09 | vs |
| 1.93 | m |

Another embodiment involves a method of making a crystalline transition metal tungstate material having the formula:

$$MW_xO_y$$

where 'M' is a metal selected from Mn, Fe, Co, Ni, V, Cu, Zn, Sn, Sb, Ti, Zr and mixtures thereof; 'x' varies from 0.35 to 2, or from 0.75 to 1.5, or from 0.8 to 1.2; 'y' is a number which satisfies the sum of the valency of M and W; the material is further characterized by a unique x-ray powder diffraction pattern showing peaks at the d-spacings listed in Table A:

TABLE A

| d(Å) | I/I$_0$ (%) |
|---|---|
| 6.20 | s |
| 3.52 | vs |
| 3.12 | vs |
| 2.74 | vs |
| 2.41 | s |
| 2.33 | s |
| 2.09 | vs |
| 1.93 | m | wherein the method comprises: forming a reaction mixture containing water, source of M, source of W, and optionally a solubilizing agent, complexing agent, chelating agent, or a mixture thereof; optionally removing a component from the reaction mixture to generate an intermediate reaction mixture wherein the component is a precipitate, or at least a portion of the water, or both a precipitate and a portion of the water; reacting the reaction mixture or the intermediate mixture at a temperature from about 25° C. to about 500° C. for a period of time from about 30 minutes to 14 days to generate the crystalline transition metal tungstate material; and recovering the crystalline transition metal tungstate material.

Yet another embodiment involves a conversion process comprising contacting a sulfiding agent with a material to generate metal sulfides which are contacted with a feed at conversion conditions to generate at least one product, the material comprising: a crystalline transition metal tungstate material having the formula:

$$MW_xO_y$$

where 'M' is a metal selected from Mn, Fe, Co, Ni, V, Cu, Zn, Sn, Sb, Ti, Zr and mixtures thereof; 'x' varies from 0.35 to 2, or from 0.75 to 1.5, or from 0.8 to 1.2; 'y' is a number which satisfies the sum of the valency of M and W; the material is further characterized by a unique x-ray powder diffraction pattern showing peaks at the d-spacings listed in Table A:

TABLE A

| d(Å) | I/I0 (%) |
|---|---|
| 6.20 | s |
| 3.52 | vs |
| 3.12 | vs |
| 2.74 | vs |
| 2.41 | s |
| 2.33 | s |
| 2.09 | vs |
| 1.93 | m |

Still another embodiment of the invention is a conversion process data system comprising: at least one processor; at least one memory storing computer-executable instructions; and at least one receiver configured to receive data of at least one unit or stream in fluid communication with, and downstream from or upstream to, a conversion process comprising at least one reaction catalyzed by at least one metal sulfide resulting from the decomposition by sulfidation of a material comprising a crystalline transition metal tungstate material having the formula:

$$MW_xO_y$$

where 'M' is a metal selected from Mn, Fe, Co, Ni, V, Cu, Zn, Sn, Sb, Ti, Zr and mixtures thereof; 'x' varies from 0.35 to 2, 'y' is a number which satisfies the sum of the valency of M and W; the material is further characterized by a unique x-ray powder diffraction pattern showing peaks at the d-spacings listed in Table A:

TABLE A

| d(Å) | I/I0 (%) |
|---|---|
| 6.20 | S |
| 3.52 | Vs |
| 3.12 | Vs |
| 2.74 | Vs |
| 2.41 | S |
| 2.33 | S |
| 2.09 | Vs |
| 1.93 | M |

Yet another embodiment is a method for collecting data from a conversion process, the method comprising receiving data from at least one sensor of at least one unit or stream in fluid communication with, and downstream from or upstream to, a conversion process the conversion process comprising at least one reaction catalyzed by at least one metal sulfide derived from the decomposition by sulfidation of a crystalline transition metal tungstate material having the formula:

$$MW_xO_y$$

where 'M' is a metal selected from Mn, Fe, Co, Ni, V, Cu, Zn, Sn, Sb, Ti, Zr and mixtures thereof 'x' varies from 0.35 to 2; 'y' is a number which satisfies the sum of the valency of M and W; the material is further characterized by a unique x-ray powder diffraction pattern showing peaks at the d-spacings listed in Table A:

TABLE A

| d(Å) | I/I0 (%) |
|---|---|
| 6.20 | s |
| 3.52 | vs |
| 3.12 | vs |
| 2.74 | vs |

TABLE A

| d(Å) | I/I0 (%) |
|---|---|
| 6.20 | s |
| 3.52 | vs |
| 3.12 | vs |
| 2.74 | vs |
| 2.41 | s |
| 2.33 | s |
| 2.09 | vs |
| 1.93 | m |

Additional features and advantages of the invention will be apparent from the description of the invention, figure and claims provided herein.

DETAILED DESCRIPTION OF THE INVENTION

The invention relates to a conversion process data system comprising at least one processor; at least one memory storing computer-executable instructions; and at least one receiver configured to receive data of at least one unit or stream in fluid communication with and downstream from or upstream to a conversion process comprising at least one reaction catalyzed by at least one metal sulfide derived from a material comprising a crystalline transition metal tungstate composition. The system may further comprise an Input/Output device to collect the data. The system may have the processor configured to evaluate the data. The system may have the processor is configured to correlate the data. The system may further comprise a transmitter to transmit a signal to the conversion process. The signal may comprise instructions. The signal may comprise instructions regarding an adjustment to a parameter. The system may further comprise collecting data from multiple systems wherein one system is the parameter data system. The processor may be configured to generate predictive information. The processor may be configured to generate quantitative information. The at least one unit may include, but is not limited to, reactors, distillation or fractionation units, treaters, collectors, storage vessels, strippers, utility units, and the like.

The invention further relates to a method for collecting data from a conversion process, the method comprising receiving data from at least one sensor of at least one unit or stream in fluid communication with and downstream from or upstream to a conversion process the conversion process comprising at least one reaction catalyzed by at least one metal sulfide derived from the decomposition by sulfidation of a crystalline transition metal tungstate material. The material has the designation UPM-18. This composition has an empirical formula:

$$MW_xO_y$$

where 'M' is a metal selected from Mn, Fe, Co, Ni, V, Cu, Zn, Sn, Sb, Ti, Zr and mixtures thereof; 'x' varies from 0.35 to 2, or from 0.75 to 1.5, or from 0.8 to 1.2; 'y' is a number which satisfies the sum of the valency of M and W.

The crystalline composition of the invention is characterized by having an extended network of M-O-M, where M represents a metal, or combination of metals listed above. The structural units repeat itself into at least two adjacent unit cells without termination of the bonding. The composition can have a one-dimensional network, such as, for example, linear chains.

The crystalline transition metal tungstate composition is further characterized by a unique x-ray powder diffraction pattern showing peaks at the d-spacings listed in Table A.

Figure 1:
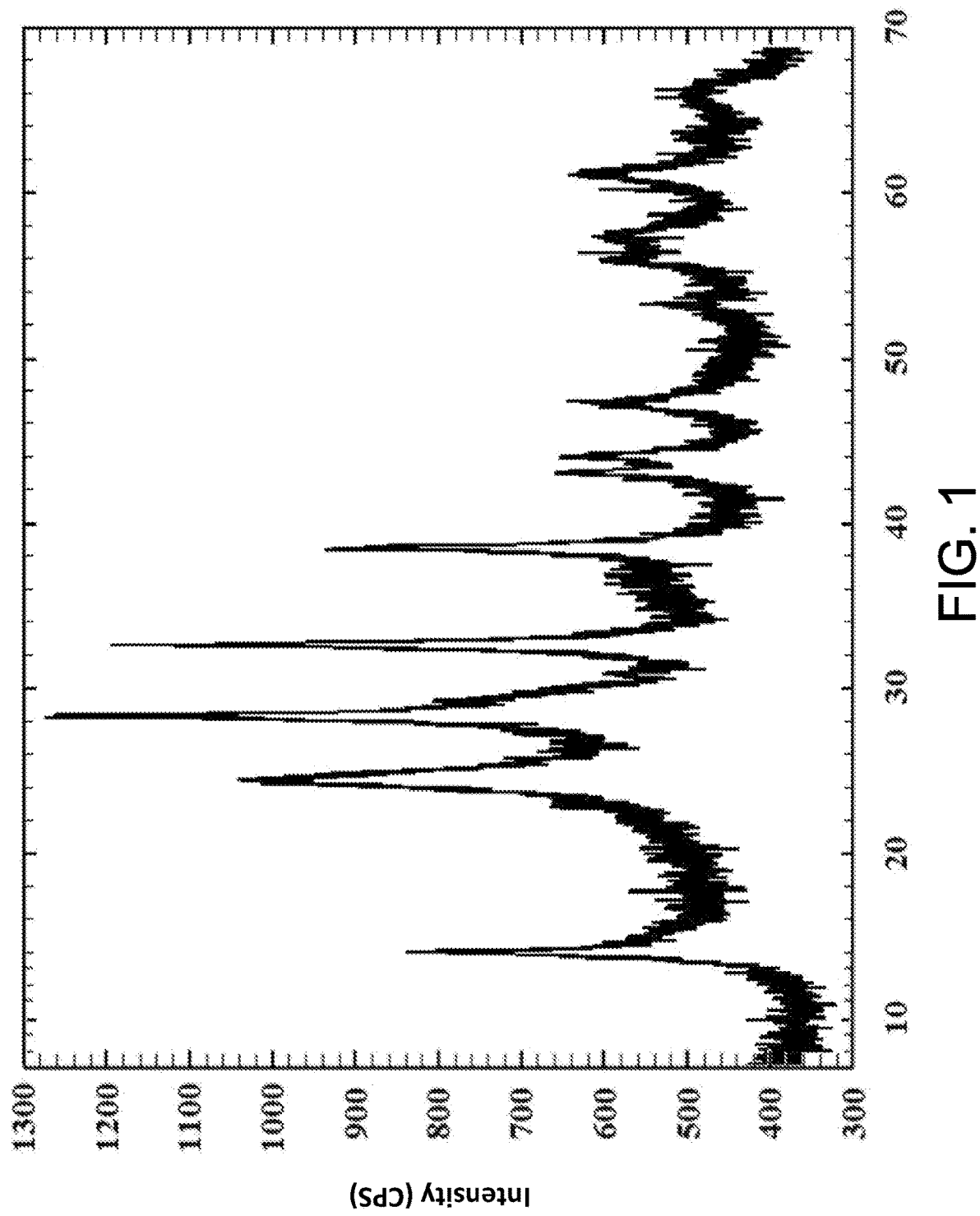
FIG. 1 is the x-ray powder diffraction pattern of a crystalline transition metal tungstate prepared as described in the Examples.

The crystalline transition metal tungstate composition of the invention is yet further characterized by the x-ray powder diffraction pattern shown in FIG. 1.

The crystalline transition metal tungstate composition can be prepared by solvothermal crystallization of a reaction mixture, typically by mixing reactive sources of tungsten with the appropriate source of metal 'M'. Depending upon the metals sources selected, the reaction mixture may optionally include a solubilizing agent "SA" in order to facilitate the dissolution of the metals. The reaction mixture may also optionally include a complexing agent, a chelating agent, or both a complexing agent and a chelating agent "CA" in order to react with the metals prior to formation of the product.

Specific examples of the tungsten source which may be utilized in this invention include but are not limited to tungsten trioxide, ammonium ditungstate, ammonium thiotungstate, ammonium heptatungstate, ammonium paratungstate, tungstic acid, tungsten oxytetrachloride, tungsten hexachloride, hydrogen tungstate, sodium ditungstate, sodium metatungstate, sodium paratungstate, and ammonium metatungstate. Sources of other metals "M" include but are not limited to the respective halide, acetate, nitrate, carbonate, thiols and hydroxide salts. Specific examples include nickel chloride, cobalt chloride, nickel bromide, cobalt bromide, zinc chloride, copper chloride, iron chloride, magnesium chloride, magnesium chloride, nickel nitrate, cobalt nitrate, iron nitrate, manganese nitrate, zinc nitrate, copper nitrate, iron nitrate, nickel acetate, cobalt acetate, iron acetate, nickel carbonate, cobalt carbonate, zinc carbonate, manganese carbonate, copper carbonate, iron carbonate, nickel hydroxide, cobalt hydroxide, manganese hydroxide, copper hydroxide, zinc hydroxide, titanium oxide, manganese oxide, copper oxide, zinc oxide, cobalt oxide, nickel oxide, iron oxide, titanium tetrachloride, tin sulfate, zinc sulfate, iron sulfate, tin chloride pentahydrate, antimony chloride, antimony acetate, vanadium chloride.

Specific examples of the optional solubilizing agent "SA" include, but are not limited to, water, organic acids such as citric acid, malic acid, maleic acid, aliphatic acids; mineral acids such as sulfuric acid, hydrochloric acid, nitric acid, phosphoric acid and boric acid. Specific examples of the optional complexing or chelating agents include, but are not limited to, ammonium hydroxide, ammonium carbonate, ammonium bicarbonate, ammonium chloride, ammonium fluoride, ethylenediaminetetraacetic acid, ethylenediamine, methylamine, dimethylamine or a combination thereof.

Generally, the solvothermal process used to prepare the composition of this invention involves forming a reaction mixture wherein all of the sources of the metal components, such as for example, Ni and W are mixed together, with the optional addition of either a solubilizing agent or a complexing agent or a chelating agent or any mixture thereof. The reaction may be at ambient temperatures or elevated temperatures. The pressure may be atmospheric pressure or autogenous pressure. The vessel used may be a closed vessel or an open vessel. Optionally, the mixture may be mixed, continuously or intermittently. In one embodiment, the reactants may be mixed intermittently at elevated temperatures. By way of specific examples, a reaction mixture may be formed which in terms of molar ratios of the oxides is expressed by the formula:

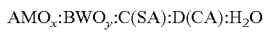

$AMO_x:BWO_y:C(SA):D(CA):H_2O$ where 'M' is selected from the group consisting of iron, cobalt, nickel, manganese, vanadium, copper, zinc and mixtures thereof; 'A' represents the molar ratio of 'M' and varies from 0.1 to 3 preferably from 0.5 to 2 or from 0.75 to 1.25; 'x' is a number which satisfies the valency of 'M'; 'B' represents the molar ratio of 'W' and varies from 0.1 to 3 preferably from 0.5 to 2 or from 0.75 to 1.25; 'y' is a number satisfies the valency of 'W'; 'C' represents the molar ratio of the optional solubilizing agent (SA) and varies from 0 to 50 or from 0.1 to 25 or from 1 to 10; represents the molar ratio of the optional complexing agent (CA) and varies from 0 to 100 or from 0.1 to 50 or from 5 to 20 the molar ratio of $H_2O$ and varies from 0.1 to 1000 or from 1 to 100 or from 2 to 20. If required, the starting reagents may be pretreated be either the addition of a complexing agent such as, but not limited to, ammonium hydroxide or citric acid. Depending upon the metal reagents selected, the pH of the mixture may be adjusted to an acidic or a basic regime. The pH of the mixture may be adjusted through the addition of a base such as $NH_4OH$, quaternary ammonium hydroxides, amines, and the like, or conversely be a mineral acid such as nitric acid, hydrochloric acid, sulfuric acid hydrofluoric acid, or an organic acid such as citric acid or malic acid, depending upon reactive sources of M. In one embodiment, the pH does not need to be adjusted.

In one embodiment, an intermediate reaction mixture may be formed by removing a component of the reaction mixture wherein the component is a precipitate, or at least a portion of the water, or both a precipitate and at least a portion of the water mixture. The intermediate may then then reacted as the reaction mixture at a temperature from about 25° C. to about 500° C. for a period of from about 30 minutes to 14 days to generate the crystalline transition metal tungstate material.

Once the reaction mixture is formed, the reaction mixture is reacted at temperatures ranging from about 25° C. to about 500° C. for a period of time ranging from 30 minutes to around 14 days. In one embodiment, the temperate range for the reaction is from about 300° C. to about 400° C. and in another embodiment the temperature is in the range of from about 100° C. to about 200° C. The temperature may be varied during the reaction period. In one embodiment, the reaction time is from about 4 to about 6 hours, and in another embodiment the reaction time is from about 4 to 7 days. The reaction is carried out under atmospheric pressure in an open vessel or in a sealed vessel under autogenous pressure. Optionally, the reaction mixture may be mixed continuously or intermittently. In one embodiment, the reaction mixture is mixed every few hours. The crystalline transition metal tungstate compositions are recovered as the reaction product. The crystalline transition metal tungstate compositions are characterized by their unique x-ray powder diffraction pattern as shown in Table A above and in the Figure.

Once formed, the crystalline transition metal tungstate composition may have a binder incorporated, where the binder may be, for example, silicas, aluminas, silica-aluminas, and mixtures thereof. The selection of binder includes but is not limited to, anionic and cationic clays such as hydrotalcites, pyroaurite-sjogrenite-hydrotalcites, montmorillonite and related clays, kaolin, sepiolites, silicas, aluminas such as (pseudo) boehomite, gibbsite, flash calcined gibbsite, eta-alumina, zicronica, titania, alumina coated titania, silica-alumina, silica coated alumina, alumina coated silicas and mixtures thereof, or other materials generally known as particle binders in order to maintain particle integrity. These binders may be applied with or without peptization. The binder may be added to the bulk crystalline transition metal tungstate composition, and the amount of binder may range from about 1 to about 30 wt % of the finished catalysts or from about 5 to about 26 wt % of the finished catalyst. The binder may be chemically bound to the crystalline transition metal tungstate composition, or may be present in a physical mixture with the crystalline transition metal tungstate composition.

At least a portion of the crystalline transition metal molybdotungstate composition, with or without a binder, or before or after inclusion of a binder, can be sulfided in situ in an application or pre-sulfided to form metal sulfides which in turn are used in an application as a catalyst. The sulfidation may be conducted under a variety of sulfidation conditions such as through contact of the crystalline transition metal molybdotungstate composition with a sulfiding agent such as sulfur-containing stream or feedstream, or a gaseous mixture of $H_2S/H_2$, or both. The sulfidation of the crystalline transition metal molybdotungstate composition may be performed at elevated temperatures, typically ranging from about 50° C. to about 600° C., or from about 150° C. to about 500° C., or from about 250° C. to about 450° C. The materials resulting from the sulfiding step, the decomposition products, are referred to as metal sulfides which can be used as catalysts in conversion processes. As noted above, at least a portion of the metal sulfides may be present in a mixture with at least one binder. The sulfiding step can take place at a location remote from other synthesis steps, remote from the location of the conversion process, or remote from both the location of synthesis and remote from location of the conversion process.

As discussed, at least a portion of the unsupported crystalline transition metal tungstate material can be sulfided and the resulting metal sulfides can be used as a catalyst or catalyst support in conversion processes such as hydrocarbon conversion processes. Hydroprocessing is one class of hydrocarbon conversion processes in which the crystalline transition metal tungstate material is useful as a catalyst. Examples of specific hydroprocessing processes are well known in the art and include hydrodenitrification, hydrodesulfurization, hydrodemetallation, hydrodesilication, hydrodearomatization, hydroisomerization, hydrotreating, hydrofining, and hydrocracking. In one embodiment, a conversion process comprises contacting the crystalline mixed transition metal tungstate with a sulfiding agent to generate metal sulfides which are contacted with a feed stream at conversion conditions to generate at least one product.

The operating conditions of the hydroprocessing processes listed above typically include reaction pressures from about 2.5 MPa to about 17.2 MPa, or in the range of about 5.5 to about 17.2 MPa, with reaction temperatures in the range of about 245° C. to about 440° C., or in the range of about 285° C. to about 425° C. Contact time for the feed and the active catalyst, referred to as liquid hour space velocities (LHSV), should be in the range of about 0.1 $h^{-1}$ to about 10 $h^{-1}$, or about 2.0 $h^{-1}$ to about 8.0 $h^{-1}$. Specific subsets of these ranges may be employed depending upon the feedstock being used. For example, when hydrotreating a typical diesel feedstock, operating conditions may include from about 3.5 MPa to about 8.6 MPa, from about 315° C. to about 410° C., from about 0.25/h to about 5/h, and from about 84 $Nm^3$ $H_2/m^3$ to about 850 $Nm^3$ $H_2/m^3$ feed. Other feedstocks may include gasoline, naphtha, kerosene, gas oils, distillates, and reformate.

Any of the lines, conduits, units, devices, vessels, surrounding environments, zones or similar used in the process or the method of making may be equipped with one or more monitoring components including sensors, measurement devices, data capture devices or data transmission devices. Signals, process or status measurements, and data from monitoring components may be used to monitor conditions in, around, and on process equipment. Signals, measurements, and/or data generated or recorded by monitoring components may be collected, processed, and/or transmitted through one or more networks or connections that may be private or public, general or specific, direct or indirect, wired or wireless, encrypted or not encrypted, and/or combination(s) thereof; the specification is not intended to be limiting in this respect.

Signals, measurements, and/or data generated or recorded by monitoring components may be transmitted to one or more computing devices or systems. Computing devices or systems may include at least one processor and memory storing computer-readable instructions that, when executed by the at least one processor, cause the one or more computing devices to perform a process that may include one or more steps. For example, the one or more computing devices may be configured to receive, from one or more monitoring component, data related to at least one piece of equipment associated with the process. The one or more computing devices or systems may be configured to analyze the data. Based on analyzing the data, the one or more computing devices or systems may be configured to determine one or more recommended adjustments to one or more parameters of one or more processes described herein. The one or more computing devices or systems may be configured to transmit encrypted or unencrypted data that includes the one or more recommended adjustments to the one or more parameters of the one or more processes or method described herein. Examples are provided below so that the invention may be described more completely. These examples are only by way of illustration and should not be interpreted as a limitation of the broad scope of the invention, which is set forth in the claims.

By way of example, sensors and measurements as to a parameter of a conversion process comprising at least one reaction catalyzed by at least one metal sulfide derived from crystalline transition metal tungstate material having the formula:

$$MW_xO_y$$

where 'M' is a metal selected from Mn, Fe, Co, Ni, V, Cu, Zn, Sn, Sb, Ti, Zr and mixtures thereof; 'x' varies from 0.35 to 2, 'y' is a number which satisfies the sum of the valency of M and W; the material is further characterized by a unique x-ray powder diffraction pattern showing peaks at the d-spacings listed in Table A:

TABLE A

| d(Å) | I/I0 (%) |
|---|---|
| 6.20 | S |
| 3.52 | Vs |
| 3.12 | Vs |
| 2.74 | Vs |
| 2.41 | S |
| 2.33 | S |
| 2.09 | Vs |
| 1.93 | M |

Such sensors or measurements may be associated with any portion or component of the conversion process. Control of one or more conversion process parameters may be employed. The data sensed and received may be used as the basis for adjustment or control of a variety of parameters such as process variables and conditions. The data may provide predictive information. Similarly, sensors and measurements as to a parameter of a method of making a crystalline transition metal tungstate material may be associated with any portion or component of the method of making. Control of one or more method of making parameters may be employed. The data sensed and received may be used as the basis for adjustment or control of a variety of parameters such as process variables and conditions. The data may provide predictive information.

Figure 2:
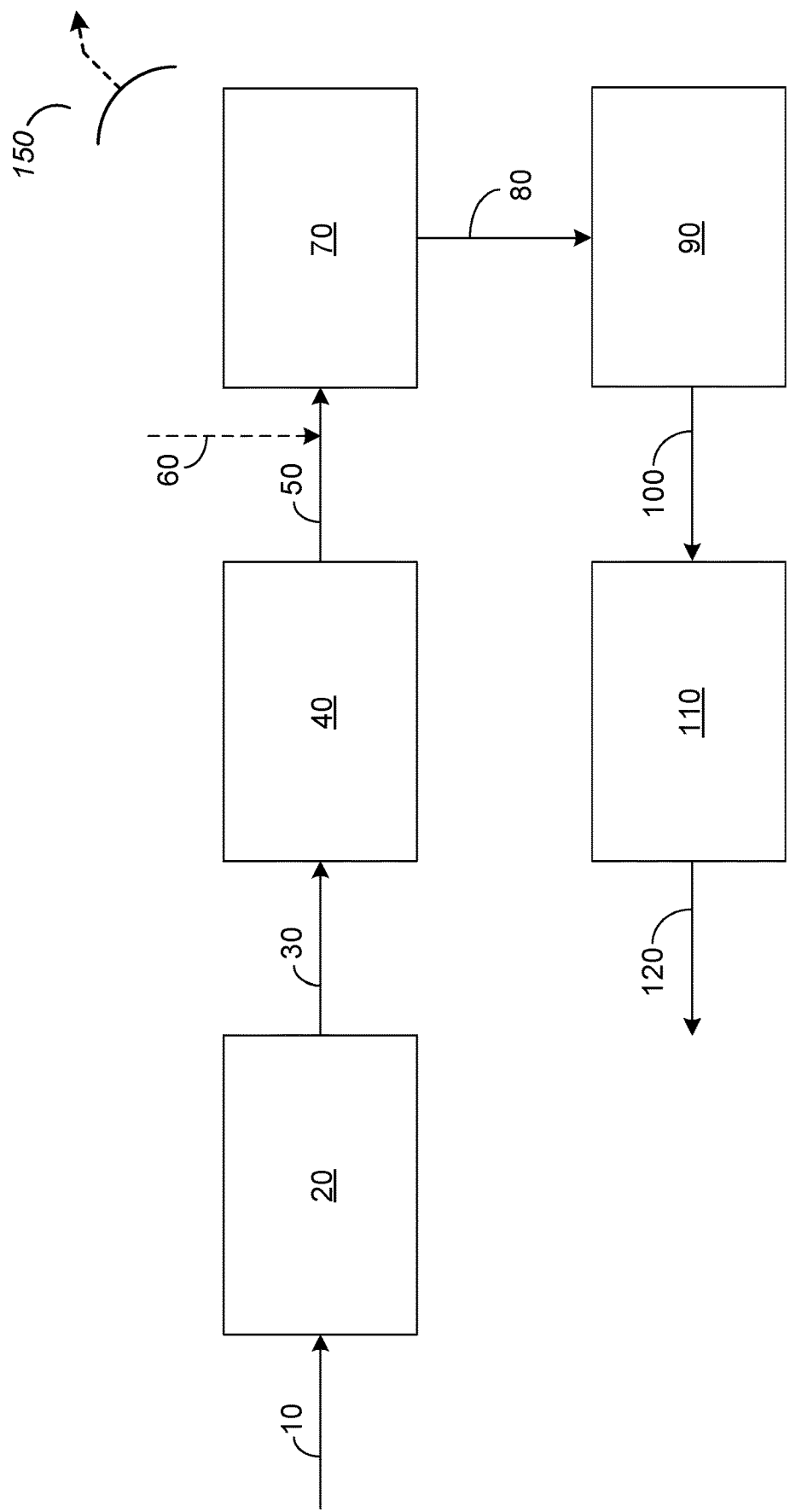
FIG. 2 illustrates a multi-unit, multi-stream process having units and streams in fluid communication with and downstream from or upstream to a conversion process using as a catalyst, the crystalline transition metal tungstate material, or metal sulfides as decomposition products thereof.

FIG. 2 illustrates a conversion process where a first feed in line 10 is introduced to a unit 20 to provide a first effluent 30. The first effluent 30 in turn is introduced into second unit 40 to generate second effluent 50. Second effluent 50 is introduced to reactor 70 to contact the catalyst contained within reactor 70 and generate a reaction product. An effluent of the reactor is removed in line 80. A sulfiding agent may be included with second effluent 50, or optionally a sulfiding agent may be introduced in line 60. The catalyst contained within reactor 70 is the catalyst described herein.

Sensors, including analytical devices, may be employed anywhere reasonable in the conversion process equipment, or method of making equipment, as well as one or more transmitter(s), shown generally as 150. Examples of the data sensed may include process and levels monitoring, catalyst monitoring, asset health monitoring, safety applications, security monitoring and access, regulatory reporting and monitoring, asset location tracking, maintenance, turnaround activities, and the like. The data sensed may be of any streams or units in fluid communication and upstream or downstream of reactor 70, and or of reactor 70.

As will be appreciated by one of skill in the art upon reading the following disclosure, various aspects described herein may be embodied as a method, a computer system, or a computer program product. Accordingly, those aspects may take the form of an entirely hardware embodiment, an entirely software embodiment or an embodiment combining software and hardware aspects. Furthermore, such aspects may take the form of a computer program product stored by one or more non-transitory computer-readable storage media having computer-readable program code, or instructions, embodied in or on the storage media. Any suitable computer-readable storage media may be utilized, including hard disks, CD-ROMs, optical storage devices, magnetic storage devices, and/or any combination thereof. In addition, various signals representing data or events as described herein may be transferred between a source and a destination in the form of electromagnetic waves traveling through signal-conducting media such as metal wires, optical fibers, and/or wireless transmission media (e.g., air and/or space).

Figure 3:
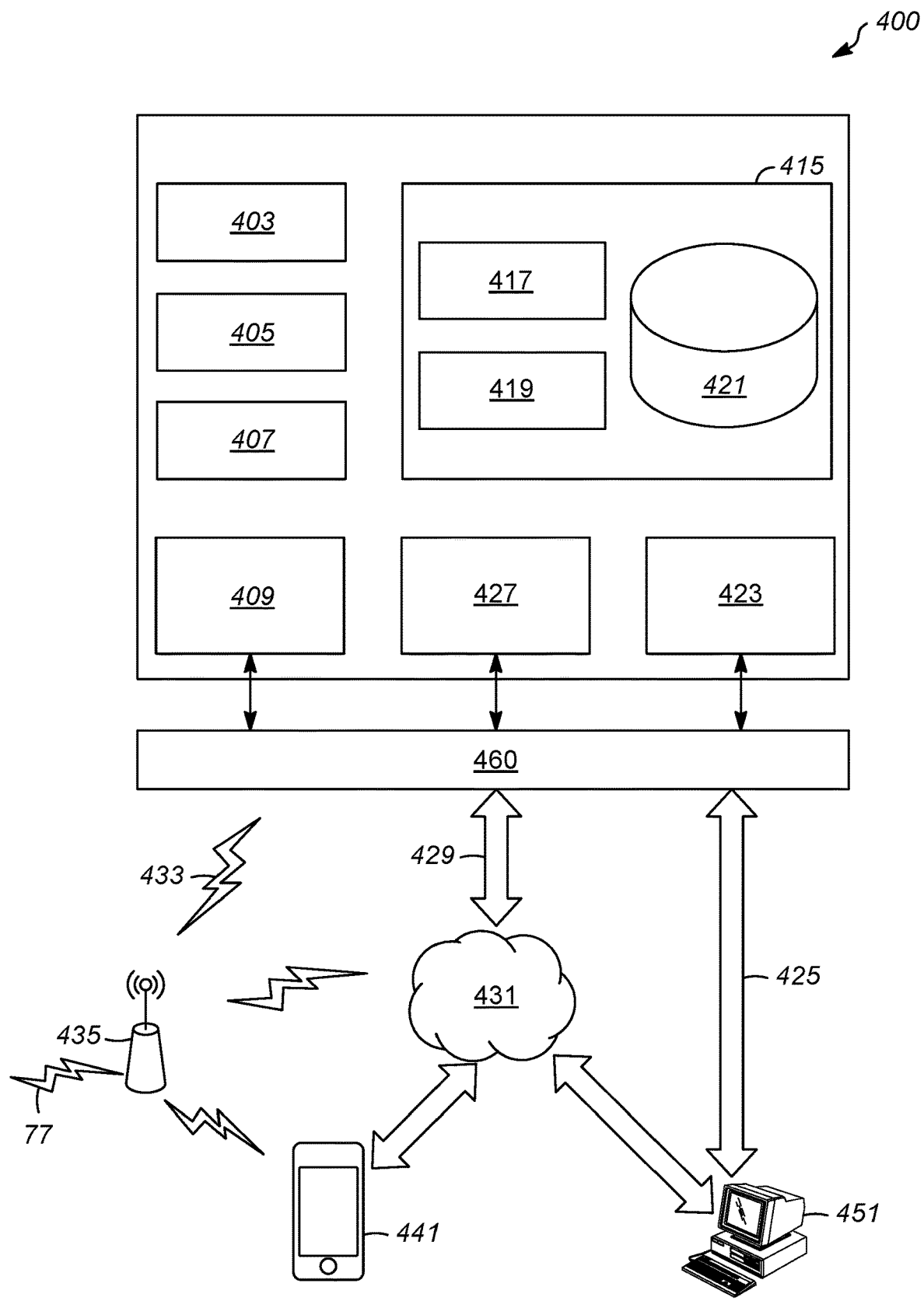
FIG. 3 shows a network environment and computing system that may be used to implement embodiments of the invention.

FIG. 3 illustrates a block diagram of a sensor data analysis system of the parameter data system 400 that may be used according to one or more illustrative embodiments of the disclosure. The parameter data system 400 may have a processor 403 for controlling overall operation of the parameter data system 400 and its associated components, including RAM 405, ROM 407, input/output module 409, and memory 415. The parameter data system 400, along with one or more additional devices (e.g., terminals 441, 451) may correspond to any of multiple systems or devices, such as mobile computing devices (e.g., smartphones, smart terminals, tablets, and the like) and/or refinery-based computing devices, configured as described herein for collecting and analyzing sensor data from devices associated with lines, vessels, or devices of one or more units, pertaining to operation or parameter of the one or more units.

Input/Output (I/O) 409 may include a microphone, keypad, touch screen, and/or stylus through which a user of the parameter data system 400 may provide input, and may also include one or more of a speaker for providing audio output and a video display device for providing textual, audiovisual and/or graphical output. Software may be stored within memory 415 and/or storage to provide instructions to processor 403 for enabling parameter data system 400 to perform various functions. For example, memory 415 may store software used by the parameter data system 400, such as an operating system 417, application programs 419, and an associated internal database 421. Processor 403 and its associated components may allow the parameter data system 400 to execute a series of computer-readable instructions to transmit or receive data, analyze data, and store analyzed data.

The parameter data system 400 may operate in a networked environment supporting connections to one or more remote computers, such as terminals/devices 441 and 451. Parameter data system 400, and related terminals/devices 441 and 451, may include devices or sensors associated with equipment, streams, or materials of a process employing streams and a reactor, including devices on-line or outside of equipment, streams, or materials, that are configured to receive and process data. Thus, the parameter data system 400 and terminals/devices 441 and 451 may each include personal computers (e.g., laptop, desktop, or tablet computers), servers (e.g., web servers, database servers), sensors, measurement devices, communication systems, or mobile communication devices (e.g., mobile phones, portable computing devices, and the like), and may include some or all of the elements described above with respect to the parameter data system 400.

The network connections depicted in FIG. 3 include a local area network (LAN) 425 and a wide area network (WAN) 429, and a wireless telecommunications network 433, but may also include other networks. When used in a LAN networking environment, the parameter data system 400 may be connected to the LAN 425 through a network interface or adapter 423. When used in a WAN networking environment, the parameter data system 400 may include a modem 427 or other means for establishing communications over the WAN 429, such as network 431 (e.g., the Internet). When used in a wireless telecommunications network 433, the parameter data system 400 may include one or more transceivers, digital signal processors, and additional circuitry and software for communicating with wireless computing devices 441 (e.g., mobile phones, short-range communication systems, telematics devices) via one or more network devices 435 (e.g., base transceiver stations) in the wireless network 433. In one embodiment, any of the sensors and transmitters 50 may communicate with receiver 435 of parameter data system 400 of FIG. 3 via 77 which may be wired or wireless communication It will be appreciated that the network connections shown are illustrative and other means of establishing a communications link between the computers may be used. The existence of any of various network protocols such as TCP/IP, Ethernet, FTP, HTTP and the like, and of various wireless communication technologies such as GSM, CDMA, Wi-Fi, and WiMAX, is presumed, and the various computing devices parameter data system components described herein may be configured to communicate using any of these network protocols or technologies.

Also, illustrated in FIG. 3 is a security and integration layer 460, through which communications may be sent and managed between the parameter data system 400 (e.g., a user's personal mobile device, a refinery-based system, external server, etc.) and the remote devices (441 and 451) and remote networks (425, 429, and 433). The security and integration layer 460 may comprise one or more separate computing devices, such as web servers, authentication servers, and/or various networking components (e.g., firewalls, routers, gateways, load balancers, etc.), having some or all of the elements described above with respect to parameter data system 400. As an example, a security and integration layer 460 of a mobile computing device, refinery-based device, or a server operated by a provider, an institution, governmental entity, or other organization, may comprise a set of web application servers configured to use secure protocols and to insulate the parameter data system 400 from external devices 441 and 451. In some cases, the security and integration layer 460 may correspond to a set of dedicated hardware and/or software operating at the same physical location and under the control of same entities as parameter data system 400. For example, layer 460 may correspond to one or more dedicated web servers and network hardware in an organizational datacenter or in a cloud infrastructure supporting a cloud-based parameter data system. In other examples, the security and integration layer 460 may correspond to separate hardware and software components which may be operated at a separate physical location and/or by a separate entity.

As discussed below, the data transferred to and from various devices of parameter data system 400 may include secure and sensitive data, such as measurement data, flow control data, concentration data, process parameter data, catalyst data, quantitative data, and instructions. In at least some examples, transmission of the data may be performed based on one or more user permissions provided. Therefore, it may be desirable to protect transmissions of such data by using secure network protocols and encryption, and also to protect the integrity of the data when stored in a database or other storage in a mobile device, analysis server, or other computing devices in the parameter data system 400, by using the security and integration layer 460 to authenticate users and restrict access to unknown or unauthorized users. In various implementations, security and integration layer 460 may provide, for example, a file-based integration scheme or a service-based integration scheme for transmitting data between the various devices in the parameter data system 400. Data may be transmitted through the security and integration layer 460, using various network communication protocols. Secure data transmission protocols and/or encryption may be used in file transfers to protect to integrity of the driving data, for example, File Transfer Protocol (FTP), Secure File Transfer Protocol (SFTP), and/or Pretty Good Privacy (PGP) encryption.

In other examples, one or more web services may be implemented within the parameter data system 400 and/or the security and integration layer 460. The web services may be accessed by authorized external devices and users to support input, extraction, and manipulation of the data (e.g., sensing data, concentration data, flow control data, etc.) between the parameter data system 400. Web services built to support the parameter data system 400 may be cross-domain and/or cross-platform, and may be built for enterprise use. Such web services may be developed in accordance with various web service standards, such as the Web Service Interoperability (WS-I) guidelines. In some examples, a flow control data and/or concentration data web service may be implemented in the security and integration layer 460 using the Secure Sockets Layer (SSL) or Transport Layer Security (TLS) protocol to provide secure connections between servers (e.g., the parameter data system 400) and various clients 441 and 451 (e.g., mobile devices, data analysis servers, etc.). SSL or TLS may use HTTP or HTTPS to provide authentication and confidentiality.

In other examples, such web services may be implemented using the WS-Security standard, which provides for secure SOAP messages using XML encryption. In still other examples, the security and integration layer 460 may include specialized hardware for providing secure web services. For example, secure network appliances in the security and integration layer 460 may include built-in features such as hardware-accelerated SSL and HTTPS, WS-Security, and firewalls. Such specialized hardware may be installed and configured in the security and integration layer 460 in front of the web servers, so that any external devices may communicate directly with the specialized hardware.

In some aspects, various elements within memory 415 or other components in parameter data system 400, may include one or more caches, for example, CPU caches used by the processing unit 403, page caches used by the operating system 417, disk caches of a hard drive, and/or database caches used to cache content from database 421. For embodiments including a CPU cache, the CPU cache may be used by one or more processors in the processing unit 403 to reduce memory latency and access time. In such examples, a processor 403 may retrieve data from or write data to the CPU cache rather than reading/writing to memory 415, which may improve the speed of these operations. In some examples, a database cache may be created in which certain data from a database 421 (e.g., an operating parameter database, a concentration database, correlation database, etc.) is cached in a separate smaller database on an application server separate from the database server. For instance, in a multi-tiered application, a database cache on an application server can reduce data retrieval and data manipulation time by not needing to communicate over a network with a back-end database server. These types of caches and others may be included in various embodiments, and may provide potential advantages in certain implementations of retrieving data, collecting data, receiving data, recording data, processing data, and analyzing data, such as faster response times and less dependence on network conditions when transmitting/receiving data.

It will be appreciated that the network connections shown are illustrative and other means of establishing a communications link between the computers may be used. The existence of any of various network protocols such as TCP/IP, Ethernet, FTP, HTTP and the like, and of various wireless communication technologies such as GSM, CDMA, Wi-Fi, and WiMAX, is presumed, and the various computer devices and system components described herein may be configured to communicate using any of these network protocols or technologies.

Additionally, one or more application programs 419 may be used by the parameter data system 400 (e.g., process software applications, device configuration software applications, control software applications, and the like), including computer executable instructions for receiving and storing data from refinery-based systems, and/or mobile computing devices, determining and configuring the mobile computing device based on the retrieved and analyzed data, and/or performing other related functions as described herein.

The processor 403 may be configured to issue or recommend a command message to adjust conditions in reactor 30. The command message may be transmitted from the parameter data system 400 in an encrypted or unencrypted message that commands one or more adjustments to conditions in reactor 30. The command may be communicated through the I/O module 409, the modem 427 or the LAN interface 423 through the security/integration layer 460 and received by a network device 435 or terminals 441, 451 in reactor 30 or the refinery comprising reactor 30 to cause adjustments or halting/starting of one or more operations in the reactor 30 or the refinery. The command message may be transmitted to a terminal 441, 451 for processing and/or execution. In an alternative embodiment, the command may be directly communicated, either wirelessly or in a wired fashion, to physical components in reactor 30 or in the refinery containing reactor 30 such that the physical components include an network device 435 to receive the commands and execute the command. Terminals 441, 451 may automatically signal execution of the command or a prompt to an operator to manually execute the adjustment. Such adjustment command messages can be transmitted back to reactor 30 to be received and executed to modify or improve performance of reactor 30.

Without further elaboration, it is believed that using the preceding description that one skilled in the art can utilize the present invention to its fullest extent and easily ascertain the essential characteristics of this invention, without departing from the spirit and scope thereof, to make various changes and modifications of the invention and to adapt it to various usages and conditions. The preceding preferred specific embodiments are, therefore, to be construed as merely illustrative, and not limiting the remainder of the disclosure in any way whatsoever, and that it is intended to cover various modifications and equivalent arrangements included within the scope of the appended claims. In the foregoing, all temperatures are set forth in degrees Celsius and, all parts and percentages are by weight, unless otherwise indicated.

It should be appreciated and understood by those of ordinary skill in the art that various other components, such as valves, pumps, filters, coolers, etc., were not shown in the drawings as it is believed that the specifics of same are well within the knowledge of those of ordinary skill in the art and a description of same is not necessary for practicing or understanding the embodiments of the present invention.

While at least one exemplary embodiment has been presented in the foregoing detailed description of the invention, it should be appreciated that a vast number of variations exist. It should also be appreciated that the exemplary embodiment or exemplary embodiments are only examples, and are not intended to limit the scope, applicability, or configuration of the invention in any way. Rather, the foregoing detailed description will provide those skilled in the art with a convenient road map for implementing an exemplary embodiment of the invention. It being understood that various changes may be made in the function and arrangement of elements described in an exemplary embodiment without departing from the scope of the invention as set forth in the appended claims.

Examples are provided below so that the invention may be described more completely. These examples are only by way of illustration and should not be interpreted as a limitation of the broad scope of the invention, which is set forth in the appended claims.

Patterns presented in the following examples were obtained using standard x-ray powder diffraction techniques. The radiation source was a high-intensity, x-ray tube operated at 45 kV and 35 mA. The diffraction pattern from the copper K-alpha radiation was obtained by appropriate computer based techniques. Powder samples were pressed flat into a plate and continuously scanned from 3° and 70° (2θ). Interplanar spacings (d) in Angstrom units were obtained from the position of the diffraction peaks expressed as θ, where θ is the Bragg angle as observed from digitized data. Intensities were determined from the integrated area of diffraction peaks after subtracting background, "$I_O$" being the intensity of the strongest line or peak, and "I" being the intensity of each of the other peaks. As will be understood by those skilled in the art the determination of the parameter 2θ is subject to both human and mechanical error, which in combination can impose an uncertainty of about ±0.4° on each reported value of 2θ. This uncertainty is also translated to the reported values of the d-spacings, which are calculated from the 2θ values. In some of the x-ray patterns reported, the relative intensities of the d-spacings are indicated by the notations vs, s, m, and w, which represent very strong, strong, medium, and weak, respectively. In terms of $100(I/I_0)$, the above designations are defined as:

w=0.01-15, m=15-60: s=60-80 and vs=80-100.

In certain instances, the purity of a synthesized product may be assessed with reference to its x-ray powder diffraction pattern. Thus, for example, if a sample is stated to be pure, it is intended only that the x-ray pattern of the sample is free of lines attributable to crystalline impurities, not that there are no amorphous materials present. As will be understood to those skilled in the art, it is possible for different poorly crystalline materials to yield peaks at the same position. If a material is composed of multiple poorly crystalline materials, then the peak positions observed individually for each poorly crystalline material would be observed in the resulting summed diffraction pattern. Likewise, it is possible to have some peaks appear at the same positions within different, single phase, crystalline materials, which may be simply a reflection of a similar distance within the materials and not that the materials possess the same structure.

Example 1

Ammonium metatungstate hydrate (25.3 g, 0.1 moles of W) was dissolved in 150 ml of DI $H_2O$, concentrated ammonium hydroxide (25 mL, 30%) was added to this solution. A second solution was prepared by adding nickel nitrate hexahydrate (43.62 g, 0.15 moles of Ni) to 150 ml of DI $H_2O$. The two solutions were slowly mixed together over with the pH of the final solution being adjusted to pH 6.8 using a mild $HNO_3$ solution. The precipitate was isolated by filtration, washed with hot water and then heat treated for using a ramp rate of 2° C. per hour until the temperature reach 400° C. The material was kept at 400° C. for 24 hours. The resulting product was analyzed by X-ray powder diffraction, and the X-ray powder diffraction pattern is shown in the Figure.

Example 2

Using a ceramic dish, ammonium hydroxide (10 ml, 30%) was added to nickel carbonate hydrate (5.07 g, 0.05 moles of Ni) over a 30 minute period. Ammonium metatungstate hydrate (12.63 g, 0.05 moles of W) was added and the resultant mixture was mixed thoroughly and then heat treated for 12 hours at 150° C. with intermittent mixing. The mixture was then heat treated further at 350° C. for 24 hours. The resulting product was analyzed by X-ray powder diffraction, and the X-ray powder diffraction pattern is shown in the Figure.

Example 3

Using a ceramic dish, nickel nitrate hexahydrate (14.54 g, 0.05 moles of Ni), zinc nitrate hexahydrate (14.87 g, 0.05 moles of Zn) and ammonium metatungstate hydrate (17.71 g, 0.07 moles of W) were added together and the resultant mixture was mixed thoroughly before being heat treated for 12 hours at 150° C. with intermittent mixing. The mixture was then heat treated further at 350° C. for 24 hours. The resulting product was analyzed by X-ray powder diffraction, and the X-ray powder diffraction pattern is shown in the Figure.

Example 4

Using a ceramic dish, nickel nitrate hexahydrate (29.75 g, 0.1 moles of Ni) and ammonium metatungstate hydrate (17.71 g, 0.07 moles of W) were added together and the resultant mixture was mixed thoroughly before being heat treated for 12 hours at 150° C. with intermittent mixing. The mixture was then heat treated further at 400° C. for 24 hours. The resulting product was analyzed by X-ray powder diffraction, and the X-ray powder diffraction pattern is shown in the Figure.

Example 5

Using a ceramic dish, nickel nitrate hexahydrate (12.35 g, 0.042 moles of Ni), copper nitrate hemi(pentahydrate) (9.9 g, 0.043 moles of Cu) and ammonium metatungstate hydrate (17.71 g, 0.07 moles of W) were added together and the resultant mixture was mixed thoroughly before being heat treated for 1 hour at 75° C. The reaction intermediate was then mixed and heated at 85° C. for an hour before being heated at 110° C. for 12 hours. The sample was then ground to a fine powder and heat treated at 200° C. for 4 hours after which time the temperature was ramped at 2° C. min$^{-1}$, held at 300° C. for 4 hours and ramped again to 400° C. and held for a further 4 hours. The resulting product was analyzed by X-ray powder diffraction, and the X-ray powder diffraction pattern is shown in the Figure.

Example 6

Nickel nitrate hexahydrate (100 g, 0.34 moles of Ni), zinc nitrate (3.63 g, 0.03 moles of Zn), ammonium metatungstate hydrate (60.5 g, 0.24 moles of W) and ammonium carbonate (82.5 g, 0.86 moles) were mixed together in a covered beaker and heated at 50° C. for 4 days with intermittent mixing. The mixture was then transferred to a ceramic dish and heated at 70° C. for 1 day, before being heated to 120° C. The mixture was then heated for 1 hour at 10° C. intervals from 120° C. to 190° C., after which the material was heated at 200° C. for 24 hrs. The resulting product was analyzed by X-ray powder diffraction, and the X-ray powder diffraction pattern is shown in the Figure.

SPECIFIC EMBODIMENTS

Embodiment 1 is a crystalline transition metal tungstate material having the formula:

$$MW_xO_y$$

where 'M' is a metal selected from Mn, Fe, Co, Ni, V, Cu, Zn, Sn, Sb, Ti, Zr and mixtures thereof; 'x' varies from 0.35 to 2, 'y' is a number which satisfies the sum of the valency of M and W; the material is further characterized by a unique x-ray powder diffraction pattern showing peaks at the d-spacings listed in Table A:

TABLE A

| d(Å) | I/I0 (%) |
|---|---|
| 6.20 | s |
| 3.52 | vs |
| 3.12 | vs |
| 2.74 | vs |
| 2.41 | s |
| 2.33 | s |
| 2.09 | vs |
| 1.93 | m |

Another embodiment is the crystalline transition metal tungstate material of embodiment 1 wherein the crystalline transition metal tungstate material is present in a mixture with at least one binder and wherein the mixture comprises up to 25 wt % binder. Another embodiment is any of the previous crystalline transition metal tungstate materials wherein the binder is selected from the group consisting of silicas, aluminas, silica-aluminas, and mixtures thereof. Another embodiment is any of the previous crystalline transition metal tungstate materials wherein M is nickel or cobalt. Another embodiment is any of the previous crystalline transition metal tungstate materials wherein M is nickel. Another embodiment is any of the previous crystalline transition metal tungstate materials wherein the crystalline transition metal tungstate material is sulfided.

Embodiment 2 is a method of making a crystalline transition metal tungstate material having the formula:

$$MW_xO_y$$

where 'M' is a metal selected from Mn, Fe, Co, Ni, V, Cu, Zn, Sn, Sb, Ti, Zr and mixtures thereof; 'x' varies from 0.35 to 2; 'y' is a number which satisfies the sum of the valency of M and W; the material is further characterized by a unique x-ray powder diffraction pattern showing peaks at the d-spacings listed in Table A:

TABLE A

| d(Å) | I/I0 (%) |
|---|---|
| 6.20 | s |
| 3.52 | vs |
| 3.12 | vs |
| 2.74 | vs |
| 2.41 | s |
| 2.33 | s |
| 2.09 | vs |
| 1.93 | m | the method comprising: (a) forming a reaction mixture containing water, source of M, source of W, and optionally a solubilizing agent, complexing agent, chelating agent, or a mixture thereof; (b) optionally removing a component from the reaction mixture to generate an intermediate reaction mixture wherein the component is a precipitate, or at least a portion of the water, or both a precipitate and a portion of the water; (c) reacting the reaction mixture or the intermediate mixture at a temperature from about 25° C. to about 500° C. for a period of time from about 30 minutes to 14 days to generate the crystalline transition metal tungstate material; and (d) recovering the crystalline transition metal tungstate material.

Another embodiment is the method of embodiment 2 wherein the recovering is by filtration or centrifugation. Another embodiment is any of the previous methods method of making the crystalline transition metal tungstate material further comprising adding a binder to the recovered crystalline transition metal tungstate material. Another embodiment is any of the previous methods method of making the crystalline transition metal tungstate material wherein the binder is selected from the group consisting of aluminas, silicas, alumina-silicas, and mixtures thereof. Another embodiment is any of the previous methods method of making the crystalline transition metal tungstate material further comprising sulfiding the recovered crystalline transition metal tungstate material. Another embodiment is any of the previous methods method of making the crystalline transition metal tungstate material wherein the reacting is conducted under atmospheric pressure or autogenous pressure. Another embodiment is any of the previous methods method of making the crystalline transition metal tungstate material further comprising intermittent mixing during the reacting. Another embodiment is any of the previous methods method of making the crystalline transition metal tungstate material wherein the temperature is varied during the reacting.

Embodiment 3 is a conversion process comprising contacting a material with a sulfiding agent to convert at least a portion of the material to metal sulfides and contacting the metal sulfides with a feed at conversion conditions to generate at least one product, wherein the material comprises a crystalline transition metal tungstate material having the formula:

$$MW_xO_y$$

where 'M' is a metal selected from Mn, Fe, Co, Ni, V, Cu, Zn, Sn, Sb, Ti, Zr and mixtures thereof; 'x' varies from 0.35 to 2; 'y' is a number which satisfies the sum of the valency of M and W; the material is further characterized by a unique x-ray powder diffraction pattern showing peaks at the d-spacings listed in Table A:

TABLE A

| d(Å) | I/I0 (%) |
|---|---|
| 6.20 | s |
| 3.52 | vs |
| 3.12 | vs |
| 2.74 | vs |
| 2.41 | s |
| 2.33 | s |
| 2.09 | vs |
| 1.93 | m |

Another embodiment is embodiment 3 wherein the conversion process is hydroprocessing. Another embodiment is any of the previous conversion processes wherein the conversion process is selected from the group consisting of hydrodenitrification, hydrodesulfurization, hydrodemetallation, hydrodesilication, hydrodearomatization, hydroisomerization, hydrotreating, hydrofining, and hydrocracking. Another embodiment is any of the previous conversion processes wherein the crystalline transition metal tungstate material is present in a mixture with at least one binder and wherein the mixture comprises up to about 25 wt % binder. Another embodiment is any of the previous conversion processes wherein the crystalline transition metal tungstate material is sulfided. Another embodiment is embodiment 3 or 2 further comprising at least one of: sensing at least one parameter of the process or method and generating a signal or data from the sensing; or generating and transmitting a signal; or generating and transmitting data.

Embodiment 4 is a conversion process data system comprising:
(a) at least one processor;
(b) at least one memory storing computer-executable instructions; and
(c) at least one receiver configured to receive data of at least one unit or stream in fluid communication with and downstream from or upstream to a conversion process comprising at least one reaction catalyzed by at least one metal sulfide resulting from the decomposition by sulfidation of a material comprising a crystalline transition metal tungstate material having the formula:

$MW_xO_y$ where 'M' is a metal selected from Mn, Fe, Co, Ni, V, Cu, Zn, Sn, Sb, Ti, Zr and mixtures thereof; 'x' varies from 0.35 to 2; 'y' is a number which satisfies the sum of the valency of M and W; the material is further characterized by a unique x-ray powder diffraction pattern showing peaks at the d-spacings listed in Table A:

TABLE A

| d(Å) | I/I0 (%) |
|---|---|
| 6.20 | S |
| 3.52 | Vs |
| 3.12 | Vs |
| 2.74 | Vs |
| 2.41 | S |
| 2.33 | S |
| 2.09 | Vs |
| 1.93 | M |

Another embodiment is embodiment 4 further comprising an Input/Output device to collect the data, or evaluate the date, or correlate the data, or any combination thereof. Another embodiment is embodiment 4 further comprising a transmitter to transmit a signal to the conversion process. Another embodiment is embodiment 4 wherein the signal comprises instructions. Another embodiment is embodiment 4 wherein the signal comprises instructions regarding an adjustment to a parameter. Another embodiment is embodiment 4 further comprising collecting data from multiple systems wherein one system is the parameter data system. Another embodiment is embodiment 4 wherein the processor is configured to generate predictive information or quantitative information. An embodiment of the invention is one, any or all of prior embodiments in this paragraph up through the fourth embodiment in this paragraph wherein the at least one unit or stream is not in direct fluid communication with the conversion process.

Embodiment 5 is a method for collecting data from a conversion process, the method comprising receiving data from at least one sensor of least one unit or stream in fluid communication with and downstream from or upstream to a conversion process, the conversion process comprising at least one reaction catalyzed by at least one metal sulfide derived from the decomposition by sulfidation of a crystalline transition metal tungstate material having the formula:

$MW_xO_y$ where 'M' is a metal selected from Mn, Fe, Co, Ni, V, Cu, Zn, Sn, Sb, Ti, Zr and mixtures thereof; 'x' varies from 0.35 to 2; 'y' is a number which satisfies the sum of the valency of M and W; the material is further characterized by a unique x-ray powder diffraction pattern showing peaks at the d-spacings listed in Table A:

TABLE A

| d(Å) | I/I0 (%) |
|---|---|
| 6.20 | s |
| 3.52 | vs |
| 3.12 | vs |
| 2.74 | vs |
| 2.41 | s |
| 2.33 | s |
| 2.09 | vs |
| 1.93 | m |

Another embodiment is embodiment 5 further comprising at least one of displaying or transmitting or analyzing the received data. Another embodiment is embodiment 5 further comprising analyzing the received data to generate at least one instruction and transmitting the at least one instruction. Another embodiment is embodiment 5 further comprising analyzing the received data and generating predictive information or quantitative information. An embodiment of the invention is one, any or all of prior embodiments in this paragraph up through the fifth embodiment in this paragraph wherein the at least one unit or stream is not in direct fluid communication with the conversion process.

Without further elaboration, it is believed that using the preceding description that one skilled in the art can utilize the present invention to its fullest extent and easily ascertain the essential characteristics of this invention, without departing from the spirit and scope thereof, to make various changes and modifications of the invention and to adapt it to various usages and conditions. The preceding preferred specific embodiments are, therefore, to be construed as merely illustrative, and not limiting the remainder of the disclosure in any way whatsoever, and that it is intended to cover various modifications and equivalent arrangements included within the scope of the appended claims.

In the foregoing, all temperatures are set forth in degrees Celsius and, all parts and percentages are by weight, unless otherwise indicated.

The invention claimed is:

1. A conversion process data system comprising:
   (a) at least one processor;
   (b) at least one memory storing computer-executable instructions; and
   (c) at least one receiver configured to receive data of at least one unit or stream in fluid communication with and downstream from, or upstream to, a conversion process comprising at least one reaction catalyzed by at least one metal sulfide resulting from the decomposition by sulfidation of a material comprising a crystalline transition metal tungstate material having the formula:

$MW_xO_y$ where 'M' is a metal selected from Mn, Fe, Co, Ni, V, Cu, Zn, Sn, Sb, Ti, Zr and mixtures thereof; 'x' varies from 0.35 to 2, 'y' is a number which satisfies the sum of the valency of M and W; the material is further characterized by a unique x-ray powder diffraction pattern showing peaks at the d-spacings listed in Table A:

TABLE A

| d(Å) | I/I0 (%) |
|---|---|
| 6.20 | S |
| 3.52 | Vs |
| 3.12 | Vs |
| 2.74 | Vs |
| 2.41 | S |
| 2.33 | S |
| 2.09 | Vs |
| 1.93 | M. |

2. The system of claim 1 further comprising an Input/Output device to collect the data, or evaluate the date, or correlate the data, or any combination thereof.

3. The system of claim 1 further comprising a transmitter to transmit a signal to the conversion process.

4. The system of claim 3 wherein the signal comprises instructions.

5. The system of claim 4 wherein the signal comprises instructions regarding an adjustment to a parameter.

6. The system of claim 1 further comprising collecting data from multiple systems wherein one system is the parameter data system.

7. The system of claim 1 wherein the processor is configured to generate predictive information or quantitative information.

8. The system of claim 1 wherein the at least one unit or stream is not in direct fluid communication with the conversion process.

* * * * *